US00PP29422P3

(12) United States Plant Patent
Sparks

(10) Patent No.: US PP29,422 P3
(45) Date of Patent: Jun. 26, 2018

(54) PECAN TREE NAMED 'TANNER'

(50) Latin Name: *Carya illinoinensis*
Varietal Denomination: Tanner

(71) Applicant: University of Georgia Research Foundation, Inc., Athens, GA (US)

(72) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days. days.

(21) Appl. No.: 14/999,825

(22) Filed: Jul. 5, 2016

(65) Prior Publication Data

US 2018/0014440 P1 Jan. 11, 2018

(51) Int. Cl.
*A01H 5/08* (2018.01)

(52) U.S. Cl.
USPC ..... Plt./153
CPC ..... *A01H 5/0825* (2013.01)

(58) Field of Classification Search
USPC ..... Plt./153
CPC ..... A01H 5/0825; A01H 5/00; A01H 5/08; A01H 5/10
See application file for complete search history.

(56) References Cited

PUBLICATIONS

Conner. University of Georgia College of Agricultural & Environmental Sciences, Cultivar Options for Georgia Orchards, retrieved on Aug. 15, 2017, retrieved from the Internet at https://www.georgiapecan.org/skins/userfiles/file/PecanVarieties.pdf pp. 1 and 30.*

Screen shot of Google search of pecan tanner university georgia on Aug. 15, 2017, one page.*

* cited by examiner

*Primary Examiner* — June Hwu
(74) *Attorney, Agent, or Firm* — Klarquist Sparkman, LLP

(57) ABSTRACT

A pecan tree distinguished by the following unique combination of characteristics: Consistent and acceptable fruit production, small fruit cluster, early nut maturity, large nut producing mammoth kernels with excellent color, and high resistance to scab fungus.

7 Drawing Sheets

Latin name of the genus and species of the plant: *Carya illinoinensis.*

Variety denomination: 'Tanner'.

BACKGROUND OF THE INVENTION

The present invention relates to a new and distinct variety of pecan tree named 'Tanner'. My new tree can be used in gardens or for commercial production of pecan nuts. This new tree was selected from seedlings grown from controlled pollination at the University of Georgia Horticulture Farm in Watkinsville, Ga., in 1995. The 'Tanner' selection resulted from crossing 'Desirable' (unpatented) as the seed parent with 'Pawnee' (unpatented) as the pollen parent (FIG. 1). The chart of FIG. 1 illustrates the most likely pedigree of the new 'Tanner' variety. The seedlings in the FIG. 1 chart are unnamed. All of the varieties in the FIG. 1 chart are unpatented, except for Starking Hardy Giant (U.S. Plant Pat. No. 1,361). The question marks in FIG. 1 after several of the pecan trees indicate that there is some uncertainty as to whether the identified tree is actually a part of the lineage of the new 'Tanner' pecan tree. The resulting tree was selected when growing in a cultivated area at Watkinsville, Ga.

BRIEF SUMMARY OF THE INVENTION

'Tanner' is distinguished from other pecan varieties known to the inventor due to the following unique combination of characteristics: Consistent and acceptable fruit production, small fruit cluster, early nut maturity, large nut producing mammoth kernels with excellent color and high resistance to scab fungus (*Fusicladosporium effusum*) and moderate resistance to black aphid (*Melanocallis caryaefoliae*). 'Tanner' will fill a niche for large nuts similar in size to 'Desirable' but with the advantage of earlier maturity and high resistance to scab.

Asexual reproduction of 'Tanner' by grafting, (top working) onto 'Desirable'/seedling pecan trees in 2009 and 2012 in Albany, Ga. and onto 'Cape Fear' (unpatented) trees in 2009 in Leary, Ga. was performed in order to evaluate these trees. Asexual reproduction of 'Tanner' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The 2001 Royal Horticultural Society (R.H.S.) Colour Chart.

BRIEF DESCRIPTION OF THE DRAWINGS

FIG. 2 is a photograph of bark of a 13 year old 'Tanner' tree; FIGS. 3 and 4 are photographs of leaves and young fruit of a six year old 'Tanner' tree; and FIG. 5 is a photograph of a five year old 'Tanner' tree.

The colors of an illustration of this type may vary with lighting and other conditions. Therefore, color characteristics of this new variety should be determined with reference to the observations described herein, rather than from these illustrations alone.

DETAILED DESCRIPTION

Botanical: The following detailed description of 'Tanner' is based on observations of the original tree growing in Watkinsville, Ga. that was about twenty-one years old and of four to six year old asexually reproduced 'Tanner' progeny growing in Albany, Ga. and Leary, Ga.

Varietal name: 'Tanner'.

Parentage:

*Seed parent*.—'Desirable'.

*Pollen parent*.—'Pawnee'.

Tree:

*Overall shape*.—Moderately upright, height to width ratio is about 1.5.

*Vigor*.—Vigorous, prolific, 'Tanner' fruited the second year after grafting (top working) onto 'Desirable' trees and has done so in subsequent years. The original 'Tanner' tree fruited 10 years from seed.

*Height*.—Of original tree. About 7.5 m.

*Width*.—Of original tree. About 5 m.

*Trunk*.—Of original tree diameter (measured ½ meter above ground level) about 0.4 m.

*Trunk bark texture*.—Scaly as mature tree.

*Trunk bark color*.—Grey (RHS 202B).

Figure 1:
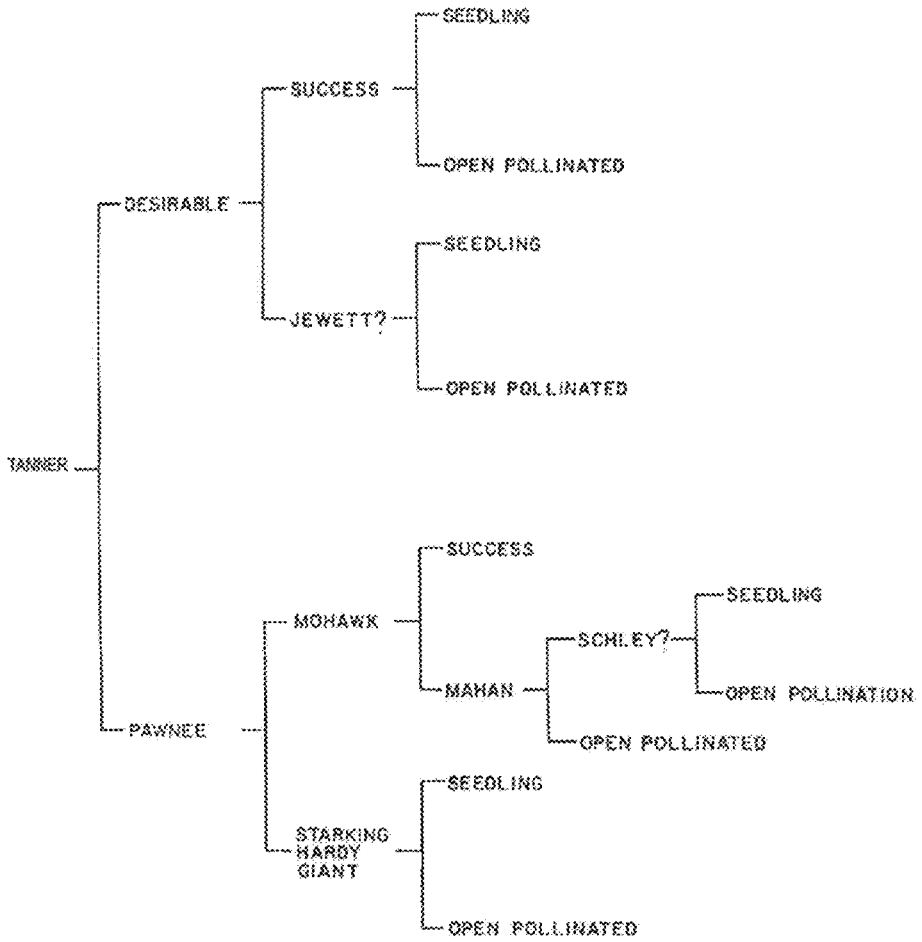
FIG. 1 is a chart showing the pedigree of 'Tanner'.
Figure 2:
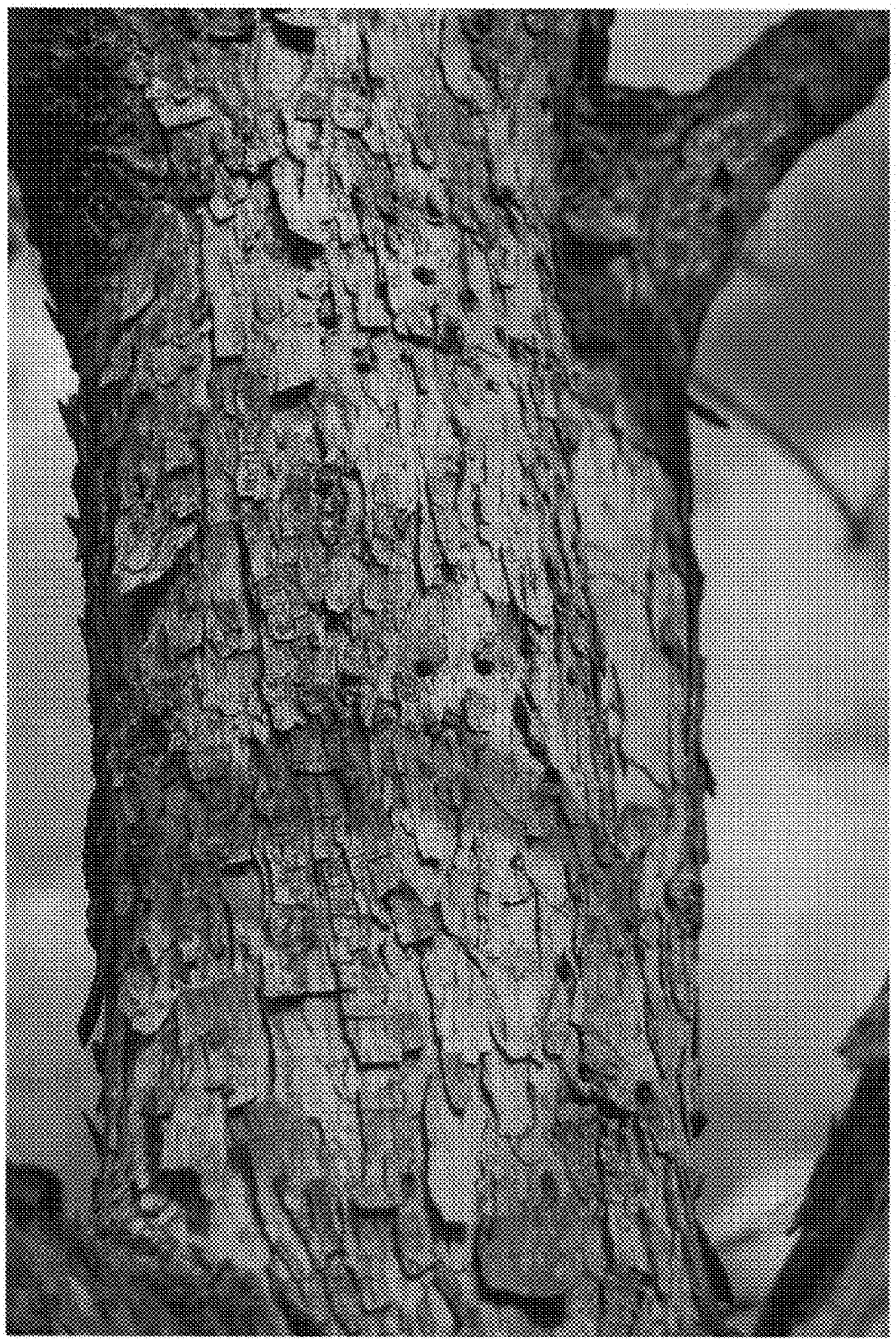
FIG. 2 is a photograph showing scaly bark of 'Tanner'.

*Patches*.—Mature trunk bark characteristically has holes pecked (FIG. 2) by yellow bellied sapsucker (*Sphyrapicus varius*).

*Branch color*.—Branch shoots in woody stage are Grey-brown (RHS 199A) in color with Grey-brown lenticels (RHS 199D) that are elongated and about 1 mm long by 0.05 mm wide.

*Internodes*.—Average length is about 1.3 cm, $3^{rd}$ and $4^{th}$ leaf from base of shoot.

*Disease and insect resistance*.—Very high resistance to scab disease. [*Fusicladosporium effusum* (G. Winters) Partridge & Morgan-Jones] and moderate resistance to black aphid *Melanocallis caryaefoliae* (Davis).

*Leaves*.—The mature leaf is odd pinnate compound, deciduous with leaflets having a forest green color (RHS 137A). Six to 13 leaves per shoot with 11 to 13 leaflets per mature leaf. Leaflets' pairs are oriented at 180° to the rachis as in 'Pawnee' but on vigorous growth they droop non curving at about 45°. Leaflet blade is flat and not convoluted (FIG. 3) except when growth is vigorous. Size of mature leaf (fourth leaf from base of shoot): 27 cm long, 20 cm wide. Petiole: Round in cross-section, tan in color (RHS 199B). Length of the peduncle of the fourth leaf from the base is about 5.2 cm. The diameter of the peduncle of the fourth leaf from the base is about 2.1 mm. Leaflet: Size and shape: Fourth leaflet on fourth leaf from base of shoot is 10.7 cm long by 2.5 cm wide. Falcate in shape. Base oblique. Leaflet margins are non-convoluted on mature trees but on young vigorous trees convolution increases from basal to apical leaves on the shoot. Texture: Upper leaf smooth. Sheen: Upper leaf glossy. Petiolule: Sessile or nearly so. Margin: Serrate. Tip shape: Acuminate and narrow. Leaflet color: Upper leaf surface: Dark green (RHS 139A). Lower leaf surface: Green (RHS 138A). Pubescence: Upper leaf surface is not pubescent. Lower leaf surface is slightly pubescent.

*Inflorescence*.—

*General*.—The 'Tanner' pecan is monoecious, anemophilous, and protandrous (Table 1).

*Flowers*.—Pistil flowers are borne on a determinate spike, with staminate flowers borne on a determinate pendulous catkin. One-six individual pistillate flowers per spike, are borne alternately on terminally-positioned spikes. The pistillate flower is symmetrical with no stamens or petals. The pedicels are sessile. The staminate or catkin length is 8.6 mm and width is 6.7 mm. The staminate color is green (RHS 144B) with gold pollen (RHS 3A). The involucre size, includes the stigma, is 5.5 mm long and 2.0 mm wide. Anthocyan on stigma is strong. The flower has one pistil with an oxblood red (RHS 61A) stigma. The flower has four bracts, which are green (RHS 144A), lanceolate, 3.4 mm long by 1.0 mm wide and are fused at the bases, forming a copular involucre.

Fruit: Mature fruit is dehiscent.

Figure 4:
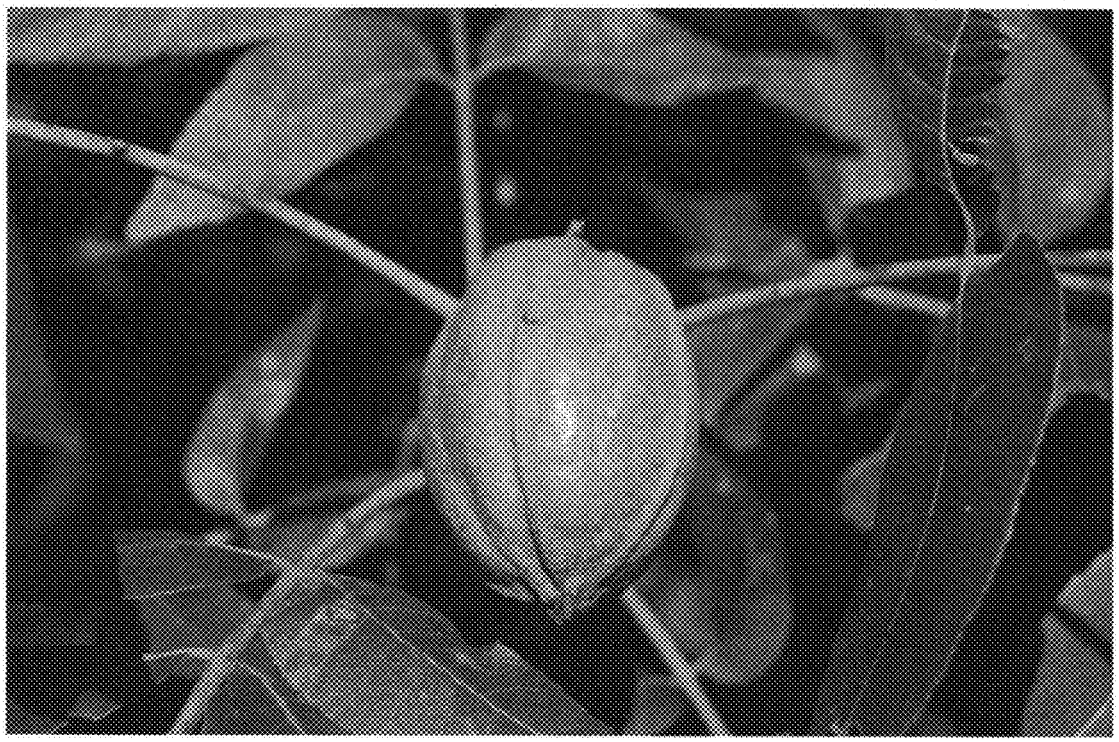
FIG. 4 is a photograph of a young fruit of 'Tanner' just before shuck dehiscence.
Figure 5:
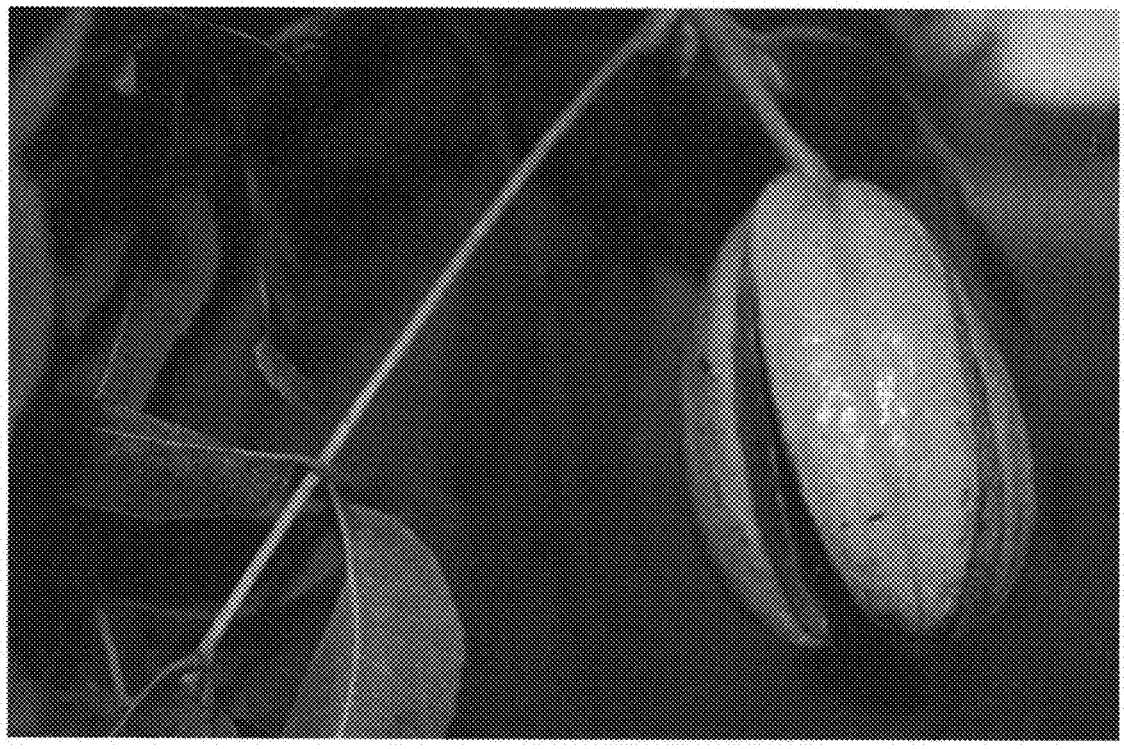
FIG. 5 is a photograph of fruit of 'Tanner' during shuck dehiscence.

*Shuck*.—Green (RHS 144B) but slightly stippled near maturity (FIG. 4). Open widely during dehiscence (FIG. 5).

*Fruit split during water stage*.—Not observed to be a problem.

*Shuck decline*.—Shuck dieback during kernel formation has not been observed to be a problem.

Nuts: (Observations from a limited number of typical nuts from several growing seasons in Albany, Leary and Watkinsville, Ga.).

*Size*.—Large, length about 45 mm, width about 27 mm (width measurement taken midway along the length of the nut and across sutures); length to width ratio about 1.7. Nut flatness (ratio of width across sutures to width between sutures) is 1.03.

*Form*.—Oblong with a round cross-section, base shape is obtuse, apex shape is acute-acute asymmetric, the apex is slightly grooved, shell suture is not elevated, shell surface is slightly ridged, otherwise shell topography is smooth.

*Dorsal grooves*.—Wide, thereby decreasing the percentage kernel in the nut.

*Ventral grooves*.—Narrow and deep.

*Weight*.—About 10.0 g per nut (non-limiting soil moisture).

*Cluster size*.—About 2.2 fruits per mature cluster.

*Shell topography*.—Faint ridges, otherwise smooth.

*Shell thickness*.—Moderately thick, 0.87 mm.

*Shell color*.—Grey-brown (RHS N199B).

*Kernel color*.—Good color, Grayed-orange (RHS 165B).

*Kernel coat*.—Occasional minute specks.

*Kernel percentage of nut*.—About 55.0 percent.

*Nut maturity*.—About September 20th.

*Harvest ability*.—Exceptionally suitable for machine harvest. Uniform maturity.

*Cracking/shelling ability*.—Cracks exceptionally well, percentage of kernels with intact halves is high. Typically, less than one percent of chipped or broken kernels were observed. When over dried, suture occasionally partially splits.

COMPARISONS TO OTHER VARIETIES

Figure 3:
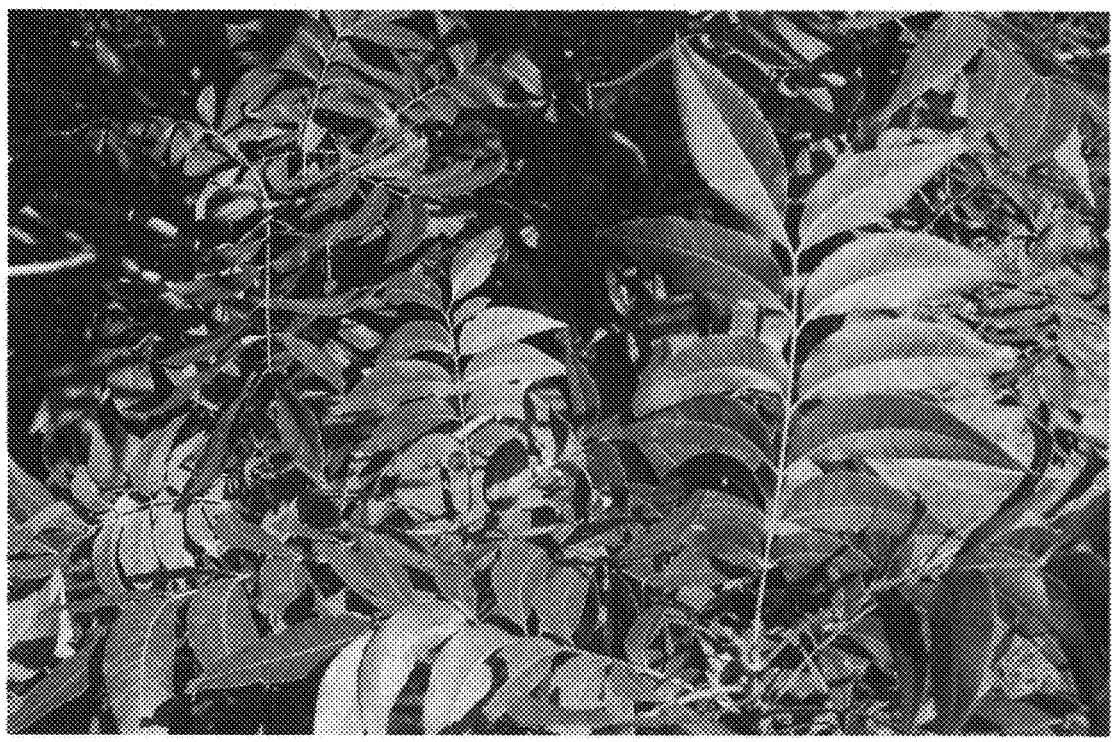
FIG. 3 is a photograph of leaf architecture of 'Tanner'.

Tree form of 'Tanner' is moderately upright in contrast to both parents and almost all other pecan cultivars. Shoot growth is long or "leggy" producing an open canopy. Thus, 'Tanner', like upright 'Whiddon' (U.S. Plant patent application Ser. No. 14/999,823) trees can be planted in higher tree density than most cultivars. The timing of bud break (Table 2) of 'Tanner' is similar to 'Whiddon', 'Tom' (U.S. Plant Pat. No. 26,705) 'Huffman' (U.S. Plant Pat. No. 25,465), 'Morrill' (U.S. Plant Pat. No. 23,335) and 'Stuart' (unpatented) pecan trees making it is less susceptible to late-spring freezes than 'Byrd' (U.S. Plant Pat. No. 20,867), 'Cunard' (U.S. Plant Pat. No. 24,373), 'Desirable' and 'Treadwell' (U.S. Plant Pat. No. 25,740). The leaves of 'Tanner' are forest green as in pollen parent 'Pawnee' but are unlike the pale green of 'Desirable'. Leaflet orientation is similar to 'Pawnee' and 'Byrd' and unlike most pecan genotypes; that is opposite leaflets are oriented at 180 degrees relative to each other. (FIG. 3). Leaflet margins on vigorous shoots are convoluted. The stigmatic surface of 'Tanner' is oxblood, similar to the oxblood color of both parents and in contrast to the green stigma of 'Wichita' (unpatented) and some other cultivars. 'Tanner', like 'Tom' and 'Huffman', is highly resistant to the scab fungus (Table 3) and contrasts with the high susceptibility of both parents and to almost all other pecan cultivars. In the humid southeastern United States, scab fungus resistance is a major attribute of 'Tanner'. Resistance to black pecan aphid is moderate and similar to 'Morrill' (Table 4). Mature bark is pecked by yellow bellied sapsucker (FIG. 2) as in 'Stuart', 'Whiddon' and 'Wichita'.

Table 1 below compares periods of pollen shedding and stigma receptivity for 'Tanner' and selected other pecan cultivars in April, 2012, Watkinsville, Ga.

TABLE 1

| | April | | | | | | | | | | | | | | | | | | | |
|---|---|---|---|---|---|---|---|---|---|---|---|---|---|---|---|---|---|---|---|---|
| | 9 | 10 | 11 | 12 | 13 | 14 | 15 | 16 | 17 | 18 | 19 | 20 | 21 | 22 | 23 | 24 | 25 | 26 | 27 | 28 | 29 |
| Protandrous cultivars | | | | | | | | | | | | | | | | | | | | | |
| 'Cheyenne' * | | | | | | | ..... | | | | | | | | | | | | | | |
| 'Desirable' * | | | ___ | ___ | ___ | | | | | | | | | ..... | | | | | | | |
| 'Tanner' | | | ___ | ___ | | | | | | | | | ..... | | | | | | | | |
| Protogynous | | | | | | | | | | | | | | | | | | | | | |
| 'Elliott' * | | | | ..... | ..... | ..... | ..... | ..... | | | | | | | | | | | | | |
| 'Schley' * | | | | ..... | ..... | | | | | | | | | | | | | | | | |
| 'Stuart' * | | | | | | | | | ..... | ..... | ..... | ..... | | | | | | | | | |

.... = Period of stigma receptivity.
___ = Period of pollen shedding.
* Unpatented Table 2 below compares bud break date for 'Byrd', 'Tom', 'Huffman', 'Morrill', 'Cunard', 'Treadwell', 'Stuart', 'Whiddon', 'Desirable' and 'Tanner' pecans. Observations were of trees growing in Watkinsville, Ga.

TABLE 2

| Cultivar | Bud break date |
|---|---|
| 'Byrd' | 3/27c |
| 'Tom' | 4/2a |
| 'Huffman' | 3/30b |
| 'Morrill' | 3/30b |
| 'Cunard' | 3/26c |
| 'Treadwell' | 3/27c |
| 'Stuart' | 3/31ab |
| 'Whiddon' | 3/30b |
| 'Desirable' | 3/27c |
| 'Tanner' | 4/1ab |

Means followed by the same letter are not statistically different, $P \leq 0.05$, $n = 5$.

Table 3 below compares fruit scab susceptibility of 'Tanner' with 'Byrd', 'Morrill', 'Cunard', 'Treadwell', 'Tom', 'Huffman' and 'Desirable' growing at two Georgia locations. In addition, 'Pawnee' has been observed to be more susceptible to scab disease than 'Tanner' when grown in Georgia.

TABLE 3

| | Fruit scab[z] | | | | |
|---|---|---|---|---|---|
| | Leary[y] | | | | Watkinsville[x] |
| Cultivar | 2011 | 2012 | 2013 | 2014 | 5 yr. mean[y] |
| 'Byrd' | 1.0b | 1.0b | 1.0b | 1.1d | 1.7bc |
| 'Morrill' | 1.0b | 1.0b | 1.0b | 1.3d | 1.8b |
| 'Cunard' | 1.0b | 1.0b | 1.0b | 2.3b | 2.3b |

TABLE 3-continued

| | Fruit scab[z] | | | | |
|---|---|---|---|---|---|
| | Leary[y] | | | | Watkinsville[x] |
| Cultivar | 2011 | 2012 | 2013 | 2014 | 5 yr. mean[y] |
| 'Treadwell' | 1.0b | 1.0b | 1.0b | 1.8c | 2.2b |
| 'Tom' | 1.0b | 1.0b | 1.0b | 1.0d | 1.0c |
| 'Huffman' | 1.0b | 1.0b | 1.0b | 1.0d | 1.0c |
| 'Whiddon' | 1.0b | 1.0b | 1.0b | 1.0d | 1.0c |
| 'Desirable' | 1.4a | 4.3a | 2.8a | 3.6a | 3.3a |
| 'Tanner' | 1.0b | 1.0b | 1.0b | 1.0d | 1.0c |

Means followed by the same letter within a column are not statistically different, P ≤ 0.05.
[z]1 = no lesions, 2 = occasional lesions, <10% of fruit with scab, 3 = lesions common on fruit and damaging, 1-50% of fruit with scab, 4 = wide spread lesions on fruit and damaging, 51-75% of fruit with scab, 5 = widespread lesions on fruit, fruit size suppressed and/aborted.
[y]n = 19, sprayed with fungicide.
[x]Years 2005, 08, 09, 10, 11, 12, sprayed with fungicide.

Table 4 below compares leaf susceptibility of 'Byrd', 'Huffman', 'Morrill', 'Cunard', 'Tom', 'Treadwell', 'Sumner' (unpatented), 'Whiddon', 'Desirable', and 'Tanner' pecans to black pecan aphids in Leary, Ga.

TABLE 4

| | Leaf rating[z] | |
|---|---|---|
| | Year | |
| Cultivar | (2011) | (2012) |
| 'Byrd' | 1.9a | 1.1c |
| 'Huffman' | 1.4b | 1.1c |
| 'Morrill' | 1.9a | 2.3a |
| 'Cunard' | 1.9a | 1.3c |
| 'Tom' | 1.2bc | 2.3a |
| 'Treadwell' | 2.1a | 1.2c |
| 'Sumner' | 1.8a | — |
| 'Whiddon' | 1.8a | — |
| 'Desirable' | 1.0c | 1.8c |
| 'Tanner' | 1.8a | 2.5a |

Means followed by the same letter are not statistically different, P ≥ 0.05%, n = 19.
[z]1 = no injury, 2 = <1% of leaves with injury, 3 = 1-10% of leaves with injury, 4 = 11-50% of leaves with injury, 5 = >50% of leaves with injury and partial defoliation.

Table 5 below compares nut characteristics of 'Treadwell', 'Byrd', 'Tom', 'Cunard', 'Morrill', 'Elliott', 'Huffman', 'Whiddon', 'Desirable', and 'Tanner' pecans. Observations were of trees growing in Albany, Ga., from 2009-2012.

TABLE 5

| Cultivar | Wt./ nut (g) | Nuts/ lbs (no.) | Nut length (mm) | Length/ width [z] |
|---|---|---|---|---|
| 'Treadwell' | 9.5de | 48d | 41.5e | 1.92b |
| 'Byrd' | 8.9e | 51c | 42.4e | 1.88bc |
| 'Tom' | 7.8f | 58b | 36.3f | 1.64e |
| 'Cunard' | 11.1b | 41f | 52.2a | 2.18a |
| 'Morrill' | 10.1cd | 46d | 49.2b | 2.07a |
| 'Elliott' | 7.1g | 64a | 32.5g | 1.39f |
| 'Huffman' | 12.2a | 37g | 44.7d | 1.65e |
| 'Whiddon' | 11.3b | 40fg | 45.2cd | 1.81bcd |
| 'Desirable' | 10.7bc | 42ef | 46.7c | 1.76cde |
| 'Tanner' | 10.0cd | 45de | 45.4cd | 1.71de |

TABLE 5-continued

| Cultivar | Nut [y] flatness | Shell thickness (mm) | Kernel (%) | Nut maturity date [x] |
|---|---|---|---|---|
| 'Treadwell' | 0.97d | 0.70cd | 62.2b | 24a |
| 'Byrd' | 1.04b | 0.51e | 62.3b | 24a |
| 'Tom' | 0.96d | 0.84a | 54.5c | 25a |
| 'Cunard' | 1.03b | 0.66cd | 62.5b | 25a |
| 'Morrill' | 1.11a. | 0.63d | 65.9a | 35b |
| 'Elliott' | 1.04b | 0.70cd | 52.0e | 38b |
| 'Huffman' | 1.03b | 0.72c | 55.5c | 33b |
| 'Whiddon' | 1.01c | 0.78b | 55.9c | 39b |
| 'Desirable' | 1.11a | 0.72c | 52.6d | 50c |
| 'Tanner' | 1.03b | 0.87a | 54.7c | 20a |

Means followed by the same letter within a column are not statistically different, P ≤ 0.05, n = 4.
[z] Length to width ratio = nut length divided by width. Width was measured midway the length of the nut and across the suture.
[y] Nut flatness = ratio of nut width across suture to width between suture. Measurement was made midway the length of the nut.
[x] Date when shuck dehiscence had occurred on 50% of the fruit, from September 1.

Pecan nuts of large size that mature early command a premium price. The price per pound normally declines as the harvest becomes later. Consequently, cultivars that exhibit early maturity at harvest are commercially important. 'Tanner' is in the early maturity class of 'Treadwell', 'Byrd', 'Tom', and 'Cunard'. 'Tanner' nut size is large (wt./nut) and greater then 'Byrd' and 'Tom', similar to 'Treadwell' and 'Desirable' and less than 'Cunard' and 'Huffman' (Table 5). Consequently, 'Tanner' kernels like 'Treadwell', 'Byrd', 'Cunard', 'Huffman', and 'Desirable' are suitable for the profitable mammoth half trade. 'Tanner' is not well suited as a replacement tree or as an inter plant in a 'Stuart'-'Schley' (unpatented)-'Desirable' orchard, a common combination in the southeastern United States. Nut maturity date of 'Tanner', like similar early maturing 'Byrd', 'Cunard', 'Treadwell', and 'Tom' is too early to allow a once over blended nut harvest of a 'Desirable' 'Stuart', and 'Schley' orchards. Color of a kernel's seed coat (lighter is preferred) and the percentage kernel of the nut also affects the selling price of pecans. 'Tanner' seed coat color is excellent (FIGS. 6 and 7), similar to 'Treadwell' and 'Tom' and better than 'Byrd' and 'Cunard'. Like 'Tom', 'Huffman' and 'Whiddon' the shuck opens widely which minimizes premature germination and promotes rapid pre harvest drying of the nut. Unlike 'Huffman' and 'Treadwell', the shuck surface is not russet. Also unlike 'Huffman', the shuck sutures are not serrated.

As can be seen from Table 5, the nut length is less than 'Cunard' and 'Morrill' and similar to 'Desirable' and 'Huffman'. General nut shape (length/width) is similar to 'Desirable', 'Whiddon', 'Huffman', 'Tom' and 'Byrd' but is less oblong than 'Treadwell', 'Cunard' and 'Morrill'. In cross-section (nut flatness), 'Tanner' nuts are near round (flatness ratio 1.03) and are similar to 'Byrd', 'Cunard', 'Elliott', and 'Huffman', but less symmetrical than 'Whiddon', 'Treadwell' and 'Tom', however more than 'Morrill' and 'Desirable'. The shell is thicker than 'Desirable' but the percentage kernel is higher than 'Desirable'. In pecan percentage kernel is a direct function of shell thickness and percentage of the shell cavity filled with kernel. The percentage kernel of 'Desirable', in spite of a thinner shell, is not greater than 'Tanner' because of a concave kernel/dorsal grooves are wide/central partition is thick which reduces the percentage of shell cavity filled with kernel. The percentage kernel of 'Tanner' nuts is higher than the industry standard, 'Desirable'.

Figure 6:
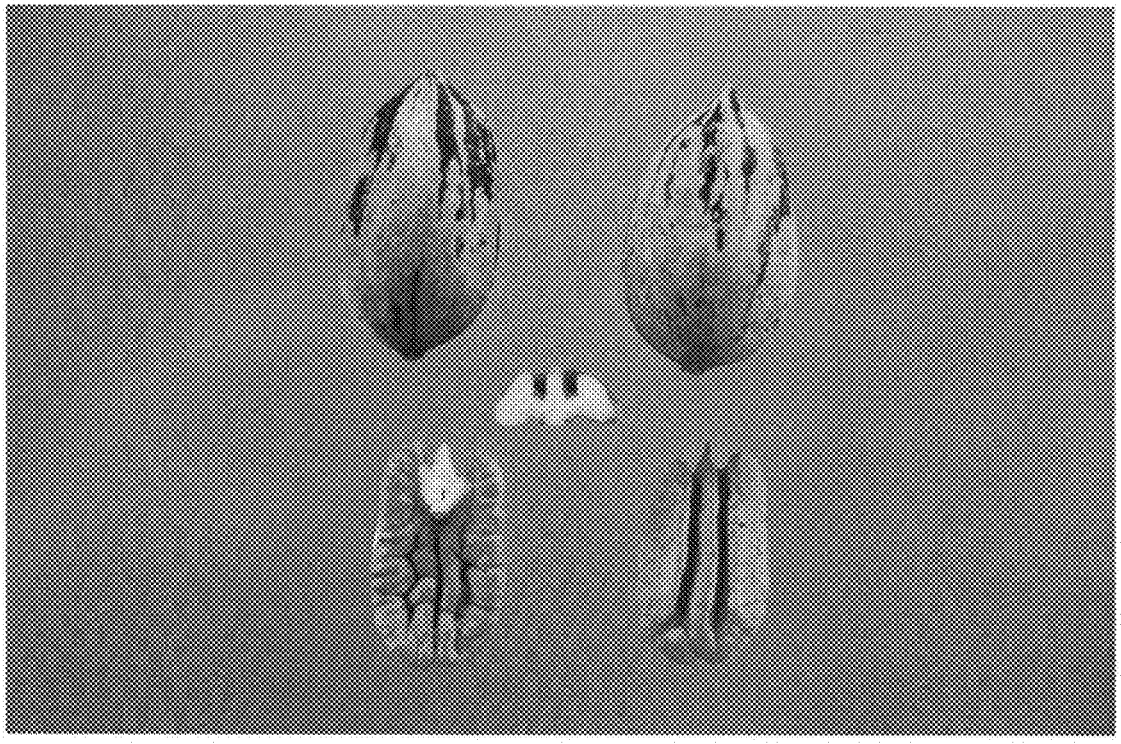
FIG. 6 is a photograph of nut shape and kernel characteristics of 'Tanner'.
Figure 7A:
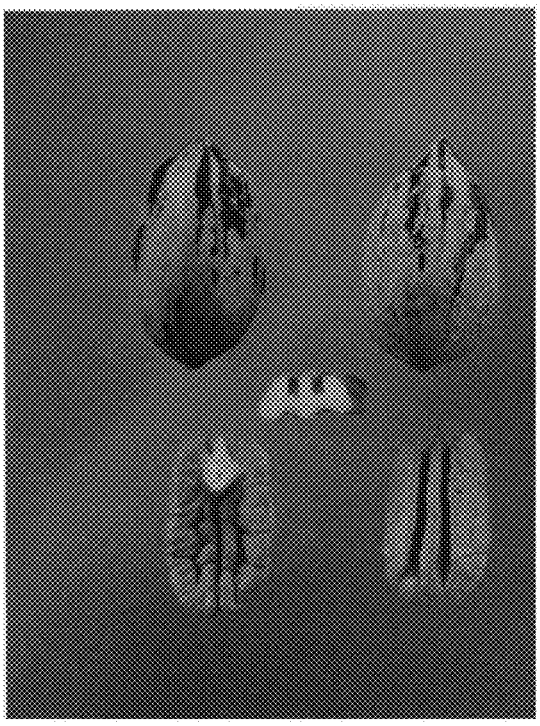
FIGS. 7A and 7B are comparison photographs of nut shape and kernel characteristics of 'Tanner' vs. 'Desirable'. The 'Tanner' nuts and kernels are shown in FIG. 7A and the 'Desirable' nuts and kernels are shown in FIG. 7B.
Figure 7B:
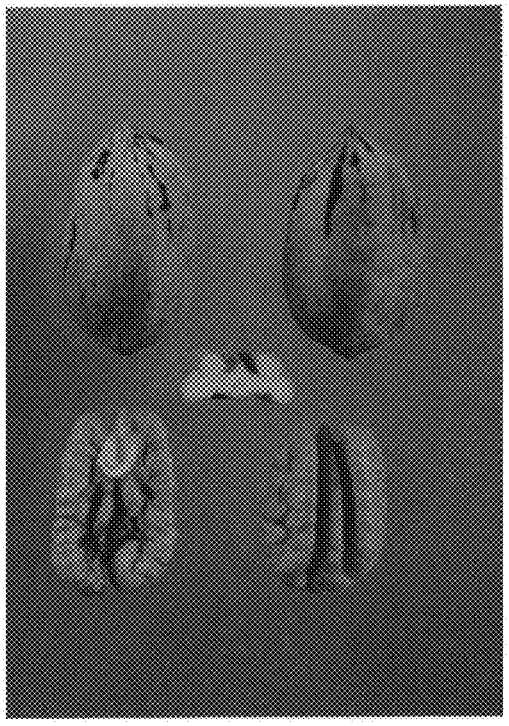
FIG. 7B PRIOR ART

Under stress, primarily fruiting stress, and when 'Pawnee' pecan trees are grown in humid southeastern United States, the kernel's seed coat can develop large conspicuous and unattractive dark spots. This speckling reduces the marketability of these nuts. This speckling has not been observed to be a problem of 'Tanner' nuts grown in Georgia. However, kernels sometimes have minute specs (FIG. 6). They differ from 'Pawnee' specking in that they are tiny and occur sparsely. A panel of growers, buyers, and processors who examined the kernels have indicated that the spots are insignificant and would have an insignificant effect on marketability and consumer preference. Kernel color is good (FIGS. 6 and 7). Kernel color retention is good. In addition, during a heavy "on" nut production year for 'Pawnee' trees growing in Georgia, kernel development is relatively poor, resulting in a high percentage of the nuts being unmarketable or of reduced value. The 'Tanner' cultivar does not have this problem.

'Tanner' is not precocious relative to 'Cunard', 'Byrd', and 'Treadwell' (Table 6). Precocity is similar to 'Desirable', 'Morrill', and 'Whiddon'. 'Tanner' is not as precocious as 'Byrd' or 'Treadwell' as is indicated by the onset of alternate fruit bearing in the third year from top working, in contrast to a lack so far of alternate fruit bearing in 'Tanner' (Table 7) as is also the case in 'Desirable', 'Huffman' and 'Tom'. Although not precocious, prolificacy as mature top worked trees is good and similar to 'Morrill', 'Huffman', and 'Tom' (Table 8). Thus, annual production is as in 'Desirable' and for the same reason, a small fruit cluster size (Table 9).

As indicated in (Table 9), the cluster size of 'Tanner' is larger than 'Desirable'. Consequently, with increasing tree maturity, alternate bearing may be more of a problem than with 'Tanner'. However, because of the small cluster size and consistent production exhibited by 'Tanner' following top working to mature pecan trees, it is expected to bear more or less consistently with increasing tree maturity as occurs with its seed parent 'Desirable'. 'Tanner' is superior to 'Desirable' in having a large nut that matures early, a higher percentage kernel, and especially important high resistance to scab disease.

Table 6 below compares Precocity of 'Cunard', 'Byrd', 'Treadwell', 'Desirable', 'Morrill', 'Tom', 'Elliott', 'Huffman', 'Whiddon', 'Stuart', and 'Tanner' pecans. Observations were of trees growing in Albany and Leary, Ga.

TABLE 6

| Cultivar | Years to initial fruiting[z] |
|---|---|
| 'Cunard' | 2 |
| 'Byrd' | 3 |
| 'Treadwell' | 3 |
| 'Desirable' | 4 |
| 'Morrill' | 4 |
| 'Elliott' | 5 |
| 'Tom' | 3 |
| 'Huffman' | 5 |
| 'Whiddon' | 4 |
| Stuart | 6 |
| 'Tanner' | 4 |

[z]Years from transplanting from the nursery.

Table 7 below compares alternate bearing tendency of 'Byrd', 'Treadwell', 'Huffman', 'Tom', 'Cunard', 'Morrill', 'Whiddon', and 'Tanner' pecans. Observations were of trees growing in Albany, Ga.

TABLE 7

| Cultivar | Years to fruiting (no.) | Years until bearing alternate (no.)[y] |
|---|---|---|
| 'Byrd' | 2 | 3 |
| 'Treadwell' | 2 | 3 |
| 'Huffman' | 2 | >6 |
| 'Tom' | 2 | >6 |
| 'Desirable' | 2 | >6 |
| 'Cunard' | 2 | 10[z] |
| 'Morrill' | 2 | >9 |
| 'Whiddon' | 2 | 4 |
| 'Tanner' | 2 | >6 |

[y]Years after top working mature trees to the respective cultivar.
Top working simulates a mature tree and allows for earlier evaluation of alternate bearing, kernel development under heavy fruit load, and suitability for mechanical harvest and ease of fruit thinning.
[z]Annual production maintained by fruit thinning.

Table 8 below compares production, weight per nut, nuts per pound, and percentage kernel of trees top worked to 'Morrill', 'Huffman', and 'Tanner' pecans. Observations were of trees growing in Albany, Ga, 2009-12.[z]

TABLE 8

| Cultivar | Lbs/tree | Wt./nut (g) | Nuts/lb. (no.) | Kernel (%) |
|---|---|---|---|---|
| 'Morrill' | 35a | 10.1b | 46b | 65.9a |
| 'Huffman' | 32a | 12.2a | 37a | 55.5b |
| 'Tanner' | 31a | 10.0b | 45b | 54.7b |

Means followed by the same letter within a column are not statistically different, $P \leq 0.05$, $n = 4$.
[z]Data are average of the second through fifth year following top working.

Table 9 below compares fruit cluster size of 'Byrd', 'Desirable', 'Huffman', 'Tom', 'Morrill', 'Pawnee', 'Cunard', 'Treadwell', 'Elliott', 'Whiddon' and 'Tanner' pecans. Observations were of trees growing in Watkinsville, Ga. Data are averages of three years, 2005, 2006, and 2008.

TABLE 9

| Cultivar | Fruits/cluster(no.)[z] |
|---|---|
| 'Byrd' | 3.1abc |
| 'Desirable' | 1.8e |
| 'Huffman' | 1.6e |
| 'Tom' | 2.8bcd |
| 'Morrill' | 2.9abcd |
| 'Pawnee' | 3.2ab |
| 'Cunard' | 3.2ab |
| 'Treadwell' | 2.7cd |
| 'Elliott' | 2.8bcd |
| 'Whiddon' | 1.8e |
| 'Tanner' | 2.2d |

Means followed by the same letter are not statistically different, $P \leq 0.05$, $n = 30$.
[z]Cluster counts made after the second drop was completed.

Under the humid growing conditions in southeastern United States, the pecan fruit is highly susceptible to splitting during the "water stage" (liquid endosperm stage) of fruit development. Fruit split can occur following rain and accompanying prolonged high humidity in early August in Georgia. Water split has not been observed in 'Tanner'.

The 'Tanner' pecan tree is therefore an improved new and distinct pecan.

I claim:

1. A new and distinct cultivar of pecan tree, as herein illustrated and described.

* * * * *